US00PP11630P

United States Patent [19]

Zaiger et al.

[11] Patent Number: Plant 11,630

[45] Date of Patent: Nov. 7, 2000

[54] PEACH TREE NAMED 'SWEET BLAZE'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 09/222,291

[22] Filed: Dec. 28, 1998

[51] Int. Cl.[7] ..... A01H 5/00

[52] U.S. Cl. ..... Plt./197

[58] Field of Search ..... Plt./197

[56] References Cited

U.S. PATENT DOCUMENTS

P.P. 9,961 7/1997 Bradford et al. ..... Plt./190

*Primary Examiner*—Howard J. Locker
*Assistant Examiner*—Melissa L. Kimball

[57] ABSTRACT

A new and distinct variety of peach tree (*Prunus persica*). The features of the tree and its fruit are characterized with the tree budded on nemaguard rootstock, grown on Hanford sandy loam soil with Storie Index rating 95, in USDA Hardiness Zone 9, near Modesto, Calif., and with standard commercial cultural fruit growing practices, such as, pruning, thinning, spraying, irrigation and fertilization. Its novelty consists of the following unique combination of features that are outstanding in a new variety:

1. Fruit with a high degree of attractive red skin color.
2. Fruit with the ability to remain firm on the tree 10 to 12 days after maturity (shipping ripe).
3. Fruit having firm flesh with good shipping and handling quality.
4. Fruit with sweet, sub-acid flavor and good eating qualities.
5. Heavy and regular production of large size fruit.
6. Vigorous, upright growth.

1 Drawing Sheet

ORIGIN OF THE VARIETY

The present new variety of peach tree was originated by us in our experimental orchard located near Modesto, Calif., as a first generation cross between two selected seedlings with field identification numbers 39EB706 and 34GA1155. The maternal parent (39EB706) originated from a cross between two selected seedlings, 32EA300 and 11E284. The seedling selection 32EA300 originated from a cross between O'Henry Peach (U.S. Plant Pat. No. 2,964) and Giant Babcock Peach (U.S. Plant Pat. No. 1,353). The seedling selection 11E284 originated from seed of an open pollinated Red Grand Nectarine (U.S. Plant Pat. No. 1,060). The pollen parent (34GA1155) originated from a seedling selection from an open pollinated May Grand Nectarine (U.S. Plant Pat. No. 2,794) crossed with a peach of unknown parentage. A large number of these first generation seedlings growing on their own root were planted and maintained under close observation, during which time one such seedling evidenced desirable tree and fruit characteristics and was selected for asexual propagation and commercialization.

ASEXUAL REPRODUCTION OF THE VARIETY

Asexual reproduction of the new and distinct variety of peach tree was by budding to Nemaguard rootstock, as performed by us in our experimental orchard located near Modesto, Calif., and shows that reproductions run true to the original tree and all characteristics of tree and the fruit are established and transmitted through succeeding asexual propagations.

SUMMARY OF THE VARIETY

The present new and distinct variety of peach tree is of large size, vigorous, upright growth; and a productive and regular bearer of large, firm, yellow flesh, clingstone fruit. The fruit is mild, sweet, sub-acid, with good flavor and eating quality. The fruit is further characterized to its novelty by its attractive red skin color, its good handling and shipping quality; and, in comparison to Sweet Scarlet Peach (U.S. Plant Pat. No. 9,695), the fruit of the new variety is approximately 18 days later in maturity.

PHOTOGRAPH OF THE VARIETY

The accompanying color photographic illustration shows typical specimens of the foliage and fruit of the present new peach tree variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTON OF THE VARIETY

The following is a detailed botanical description of the new variety of peach tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large. Tree is maintained by pruning to 12 to 14 feet in height and 12 to 14 feet in width for economical harvesting.

*Vigor.*—Vigorous. Growing 6 to 7 feet in height the first growing season. Primary scaffolds are selected and the tree is pruned to a height of 4 to 5 feet the first dormant season, this will promote proper tree growth for secondary scaffolds to be selected during pruning in the second dormant season.

*Growth.*—Upright, usually pruned to vase shape.

*Productivity.*—Productive. Fruit set is 1½ or more times the amount desirable for normal tree crop load.

*Bearer.*—Regular. Fruit must be thinned and spaced to reduce crop load to the number that will make desirable market size. The number of fruit desired per tree varies with the age of the tree, tree spacing, cultural practices, soil type and climatic conditions.

*Density.*—Medium dense. Shoot and leaf growth restrict sunlight and air movement in the center of the tree. Selective pruning to vase shape allows more sunlight and air movement to the center of the tree which will enhance fruit skin color and produce fruit with higher Brix and help keep fruit wood healthy.

*Hardiness.*—Winter chilling requirement is approximately 900 hours below 45° F. Hardiness tested only in USDA Hardiness Zone 9.

Trunk:

*Size.*—Medium to large.

*Texture.*—Medium rough.

*Color.*—Brown to tobacco brown (5-E-5) to (5-F-5).

Branches:

*Size.*—Medium.

*Texture.*—Smooth to medium shaggy. Varies with age of growth.

*Lenticels.*—Medium size. Medium number.

*Color.*—Light brown to brown (5-E-4) to (5-E-6), varies with age of growth.

Leaves:

*Size.*—Large. Average length 6½ inches. Average width 1½ inches.

*Form.*—Lanceolate. Pointed.

*Margin.*—Crenate.

*Thickness.*—Medium.

*Surface.*—Smooth.

*Petiole.*—Medium length ½ inch. Medium thickness.

*Glands.*—Reniform. Number varies from 1 to 5. Average number 3. Medium size. Located on upper portion of the petiole and lower portion of the leaf blade.

*Color.*—Upper surface — green to dark green (28-F-6) to (28-F-8). Lower surface — dull green to grayish green (28-E-7) to (28-E-8).

Flower buds:

*Size.*—Large.

*Length.*—Medium.

*Form.*—Plump.

*Pubescence.*—Pubescent.

Flowers:

*Size.*—Large, showy. Average diameter 1¼ inches.

*Pollen.*—Present, self-fertile.

*Blooming period.*—Date of First Bloom Feb. 27, 1997. Date of Last Bloom Mar. 5, 1997. Varies slightly with climatic conditions.

*Color.*—Pink to light pink (11-A-2) to (11-A-3). Pink fades to light pink with age of flowers.

Fruit:

*Maturity when described.*—Firm ripe.

*Date of first picking.*—Jun. 16, 1997.

*Date of last picking.*—Jun. 24, 1997. Varies slightly with climatic conditions.

*Size.*—Large. Average diameter axially — 2¾ to 2⅞ inches. Average transversely in suture plane — 2⅞ to 3 inches. Average weight 212 grams. Weight varies from 204 grams to 220 grams.

*Form.*—Nearly globose.

*Suture.*—Shallow, extends from base to apex.

*Ventral surface.*—Rounded.

*Apex.*—Usually rounded, varies from rounded to slight apical tip.

*Base.*—Retuse.

*Cavity.*—Rounded to slightly elongated in suture plane. Average depth ½ inch. Average breadth ¾ inch.

Flesh:

*Ripen.*—Evenly.

*Texture.*—Firm.

*Fibers.*—Small, tender.

*Aroma.*—Slight.

*Amygdalin.*—Undetected.

*Eating quality.*—Good.

*Flavor.*—Good, mild, sweet, sub-acid.

*Juice.*—Moderate amount, sweet, sub-acid, enhances flavor. Average Brix 9.8°. Brix varies with amount of crop load on the tree and climatic conditions.

*Color.*—Yellow to dark yellow (4-A-6) to (4-A-8). Pit cavity has very slight amount of red to deep red (10-A-8) to (10-C-8). Very slight bleeding of red from pit cavity into flesh.

Stem:

*Size.*—Medium. Average length ⅜ inch. Average width ⅛ inch. Enlarged at point of fruit attachment.

Skin:

*Thickness.*—Medium.

*Texture.*—Medium, tenacious to the flesh.

*Down.*—Moderate.

*Tendency to crack.*—None.

*Color.*—Yellow to vivid yellow ground color (3-A-6) to (3-A-8). Overspread with red to garnet red (10-C-6) to (10-D-8). Fruit with more exposure to sunlight have a greater degree of enhanced red skin color.

Stone:

*Type.*—Clingstone at firm ripe, semi-freestone at soft ripe maturity.

*Size.*—Large. Average length 1½ inches. Average width 1 inch. Average thickness ¾ inch.

*Form.*—Obovoid.

*Base.*—Usually straight, varies from straight to rounded.

*Apex.*—Usually acuminate, varies from acuminate to rounded.

*Surface.*—Furrowed toward apex, pitted toward base, both pits and furrows relatively deep. Pits vary from round to elongated. Ridges are relatively wide at surface of stone.

*Sides.*—Equal to unequal. On some stones one half is slightly larger in size extending farther from the suture plane.

*Tendency to split.*—None.

*Color.*—Brown to reddish brown (8-E-5) to (8-E-8).

Use: Desert.

*Market.*—Local and long distance.

Keeping quality:

*Good.*—Flesh texture remains firm after 14 days in cold storage.

Shipping quality:

*Good.*—Minimal bruising of flesh or skin scarring during picking and shipping trials.

The present new variety of peach tree, its flowers, foliage and fruit herein described may vary in slight detail due to climate, soil conditions and cultural practices under which the variety may be grown. The present description is that of the variety grown under the ecological conditions prevailing near Medesto, Calif.

We claim:

1. A new and distinct variety of peach tree, substantiallky as illustrated and described, characterized by its large size, vigorous, upright growth; and a productive and regular bearer of large, clingstone fruit that has an attractive red skin color and a mild, sweet, sub-acid flavor; and the fruit is further characterized by having firm, yellow flesh with good handling and shipping qualities, and, in comparison to Sweet Scarlet Peach (U.S. Plant Pat. No. 9,695), the fruit of the new variety is approximately 18 days later in maturity.

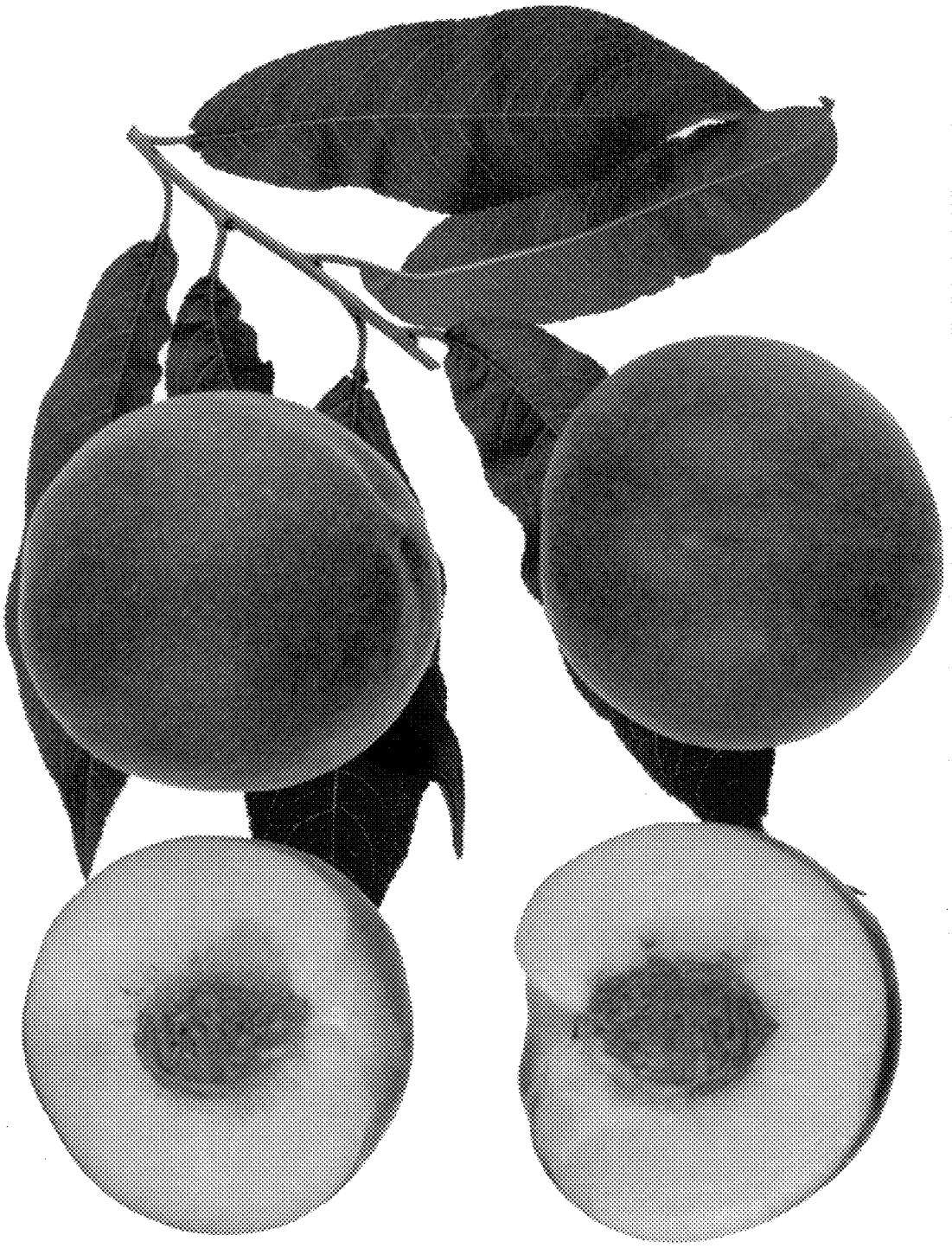

* * * * *